(12) United States Patent
Suzuki et al.

(10) Patent No.: US 7,022,863 B2
(45) Date of Patent: Apr. 4, 2006

(54) PRODUCTION METHOD OF PYRROLIDONE CARBOXYLIC ACID AND SALT THEREOF

(75) Inventors: Yuichi Suzuki, Kawasaki (JP); Ryosuke Yumioka, Kawasaki (JP); Tatsuru Tabobashi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 36 days.

(21) Appl. No.: 10/198,571

(22) Filed: Jul. 19, 2002

(65) Prior Publication Data

US 2003/0018202 A1 Jan. 23, 2003

(30) Foreign Application Priority Data

Jul. 19, 2001 (JP) ............................. 2001-219551

(51) Int. Cl.
*C07D 207/28* (2006.01)
(52) U.S. Cl. ..................................... 548/534
(58) Field of Classification Search ................. 548/534
See application file for complete search history.

(56) References Cited

U.S. PATENT DOCUMENTS 3,235,563 A 2/1966 Noyori et al.
4,946,968 A 8/1990 Krimmer et al.

FOREIGN PATENT DOCUMENTS

| GB | 834650 | 5/1960 |
| GB | 1006728 | 10/1965 |
| JP | 51110559 | * 9/1976 |
| JP | 11-342379 | 12/1999 |

OTHER PUBLICATIONS

English abstract of Journal of the Serbian Chemical Society, vol. 54(1), pp. 11-15 (1989).
English abstract of Zhejiang Gongye Daxue Xuebao, vol. 27(1), pp. 28-33 (1999).

* cited by examiner

*Primary Examiner*—Joseph K. McKane
*Assistant Examiner*—Rebecca Anderson
(74) *Attorney, Agent, or Firm*—Oblon, Spivak, McClelland, Maier & Neustadt, P.C.

(57) ABSTRACT

The present invention provides a production method of pyrrolidone carboxylic acid or a salt thereof, which includes bringing glutamic acid or a salt thereof into contact with high-temperature high-pressure water having a temperature of above 100° C. and not higher than 300° C., and a pressure higher than the vapor pressure of water at this temperature. The present invention affords efficient production and supply of pyrrolidone carboxylic acid or a salt thereof from glutamic acid or a salt there.

10 Claims, 4 Drawing Sheets

PRODUCTION METHOD OF PYRROLIDONE CARBOXYLIC ACID AND SALT THEREOF

TECHNICAL FIELD OF THE INVENTION

The present invention relates to a method for producing pyrrolidone carboxylic acid (i.e., 5-pyrrolidone-2-carboxylic acid) or a salt thereof from glutamic acid or a salt thereof. More particularly, this invention relates to a method for producing pyrrolidone carboxylic acid or a salt thereof in a short time at a high reaction rate by reacting glutamic acid or a salt thereof using high-temperature high-pressure water under a pressure condition of not lower than the vapor presure.

BACKGROUND OF THE INVENTION

Pyrrolidone carboxylic acid and salts thereof are important compounds used for various fields such as cosmetics and toiletry goods.

Pyrrolidine carboxylic acid and salts thereof are synthesized by heating for self-cyclization of glutamic acid or a salt thereof. For the reaction, glutamic acid or a salt thereof is directly heated or, upon dissolution or dispersion in water, heated to a high temperature of not lower than the boiling point of water in an autoclave (heating furnace).

For example, DE3735263 discloses a method for producing pyrrolidone carboxylic acid while maintaining the optical activity of glutamic acid, which comprises heating a salt of glutamic acid to produce a salt of pyrrolidone carboxylic acid, and desalting the salt using an ion exchange resin. This method is useful for producing a completely optically active pyrrolidone carboxylic acid salt or pyrrolidone carboxylic acid from an optically active glutamic acid salt. However, in consideration of the aspects of cost and the like, the fact that a fused reaction product solidifies as it cools during the production, making its handling difficult, and the long reaction time (fusion starts in 5 minutes and the reaction ends in 1 hour) described in an example of this patent, this method is not necessarily an advantageous production method to afford high industrial productivity.

JP-b-37-17959 describes a conventional technique comprising heating L-glutamic acid to 190–200° C. for dissolution and removing the resulting water to give pyrrolidone carboxylic acid, and further heating the acid to give ate. As described in this reference, in this method seemingly simple and industrially advantageous, a fused product becomes starch syrup during the reaction and, after cooling, becomes extremely stiff, making handling of the reaction product difficult. This publication discloses, therefore, a production method of DL-pyrrolidone carboxylic acid, which comprises heating 1 part of a D-isomer or L-isomer of glutamic acid, or DL-glutamic acid in an autoclave (heating furnace) with 0.5–15 parts of water to produce a D-isomer or L-isomer of pyrrolidone carboxylic acid in the early stage of reaction, continuing heating to give a racemate, and precipitating and separating crystals.

JP-A-51-110559 discloses a method for obtaining an aqueous solution of a salt of pyrrolidone carboxylic acid, which comprises heating a mixture of glutamic acid and a salt thereof in water under pressurization in an autoclave (heating furnace) and, after completion of the reaction, neutralizing the reaction mixture.

For the production of pyrrolidone carboxylic acid and a pyrrolidone carboxylic acid salt, a method comprising directly heating glutamic acid or a salt thereof without a solvent is known, but in consideration of difficult handling of the fused reaction product, a method comprising reaction in an aqueous solution or aqueous dispersion of glutamic acid or a salt thereof in an autoclave (heating furnace) under the vapor pressure has been actually employed.

From the aspect of industrial production, however, a reaction in an autoclave is not fully satisfactory for producing pyrrolidone carboxylic acid in a short time at a high reaction rate and higher production efficiency.

In addition, JP-A-11-342379 discloses production of various organic acids by hydrolysis of protein in fish meat with subcritical water, which produces pyrrolidone carboxylic acid as well.

However, the reaction mixture obtained by the method described in this publication contains many other amino acids and organic acids. When efficiently producing pyrrolidone carboxylic acid having a high purity, therefore, respective unit operations, such as separation by ion exchange resin and membrane and crystallization, are essential and this method is not effective.

SUMMARY OF THE INVENTION

In the above-mentioned background of the conventional art, the present invention aims at providing, in the production of pyrrolidone carboxylic acid or a salt thereof from glutamic acid or a salt thereof, a production method capable of economically producing pyrrolidone carboxylic acid or a salt thereof in a short time in a high yield by the use of economical water alone for purification.

As a result of intensive studies in an attempt to achieve the above-mentioned object, the present inventors have found that a treatment of glutamic acid or a salt thereof in contact with high-temperature high-pressure water affords production of pyrrolidone carboxylic acid or a salt thereof in a short time in a high yield, and completed the present invention.

Accordingly, the present invention provides the following.

[1] A production method of pyrrolidone carboxylic acid or a salt thereof, which comprises bringing glutamic acid or a salt thereof into contact with high-temperature high-pressure water having a temperature of above 100° C. and not higher than 300° C., and a pressure higher than the vapor pressure of water at said temperature.

[2] The production method of [1], wherein the above-mentioned glutamic acid or a salt thereof is an L-isomer, and the obtained pyrrolidone carboxylic acid or a salt thereof is an L-isomer and has an optical purity of not less than 80%.

DETAILED DESCRIPTION OF THE INVENTION

Figure 1:
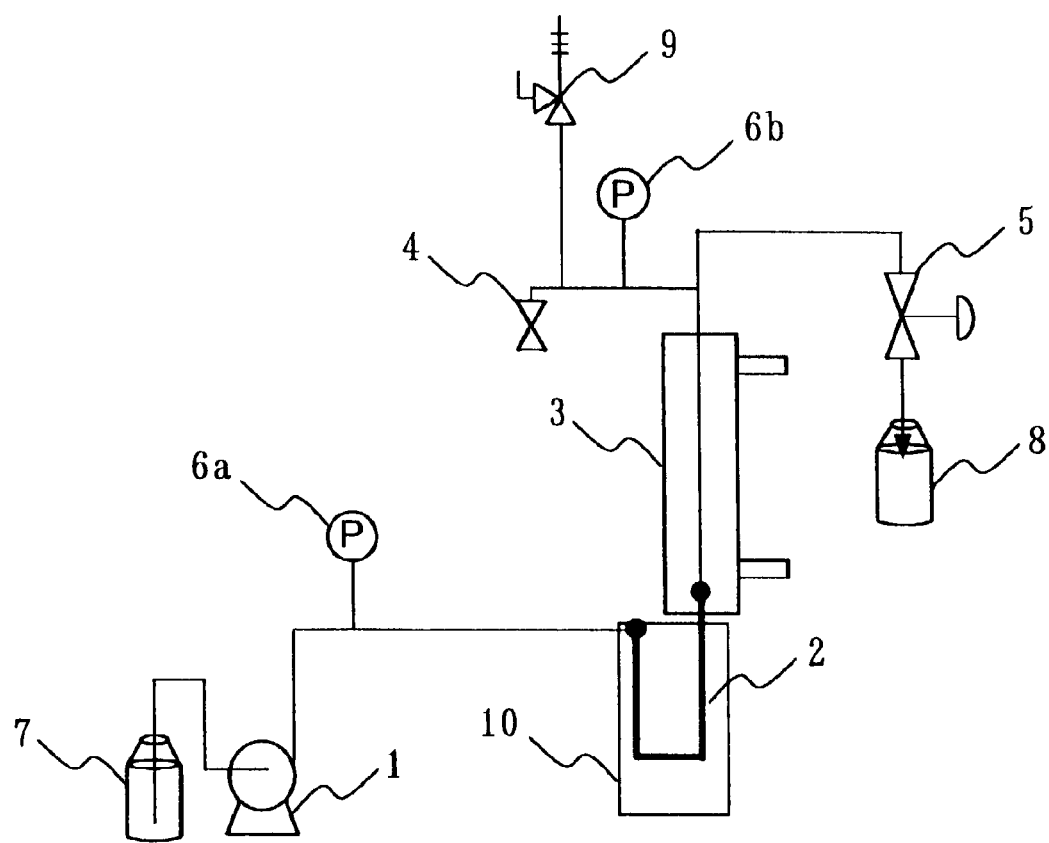
FIG. 1 is a schematic showing of the apparatus formed to practice the present invention, wherein 1 shows a high pressure pump, 2 shows a reactor, 3 shows a double pipe heat-exchanger, 4 shows a drain valve, 5 shows a back pressure valve, 6a and 6b show pressure gauges, 7 shows a feed tank, 8 shows a sampler, 9 shows a safety valve and 10 shows a heater.

In the present invention, a concrete method of reacting glutamic acid or a salt thereof by the use of high-temperature high-pressure water includes placing glutamic acid or a salt thereof in contact with high-temperature high-pressure water.

By the high-temperature high-pressure water in the present invention is meant water having a temperature of above 100° C. and up to 300° C. and a pressure higher than the vapor pressure of water at that temperature.

The above-mentioned high-temperature high-pressure water may be adjusted at least to the above-mentioned range of temperature and pressure. For easy adjustment, the temperature is preferably above 100° C. and up to 300° C. and the pressure is above 0.1 MPa and up to 25 MPa (provided that the pressure is higher than the vapor pressure of water at said temperature), more preferably, the temperature is 150° C.–300° C., most preferably 180–280° C., and the pressure is more preferably 0.5 Mpa–10 MPa.

In the production method of pyrrolidone carboxylic acid or a salt thereof of the present invention, while the contact time between glutamic acid or a salt thereof and the above-mentioned high-temperature high-pressure water (i.e., reaction time or residence time) is important, the contact time is set according to the temperature and pressure of the reaction. Preferable contact time corresponding to each temperature and pressure can be easily set when the relationship between the contact time for the above-mentioned high-temperature high-pressure water and the produced pyrrolidone carboxylic acid or a salt thereof is examined by preliminary experiments for each temperature and pressure.

In general, when the contact time of an L-isomer or D-isomer of glutamic acid or a salt thereof and high-temperature high-pressure water is suitably set, an L-isomer or D-isomer of pyrrolidone carboxylic acid or a salt thereof is produced, and when the reaction is extended, a racemate, or a DL-isomer of pyrrolidone carboxylic acid, or a salt thereof is produced. For example, when L-pyrrolidone carboxylic acid or a salt thereof is the objective product, the temperature is set for 200° C. and the pressure is set for 5 MPa, the contact time is generally 10–600 sec, preferably 20–500 sec, more preferably 40–400 sec. As a result, an L-isomer having an optical purity of not less than 80% (preferably not less than 90%) can be obtained.

The glutamic acid or a salt thereof to be used as a starting material may be an L-isomer or D-isomer of glutamic acid or a salt thereof, or a DL-isomer of glutamic acid or a salt thereof. Specific examples of the salt of glutamic acid include mono- or di-salts, such as sodium glutamate, potassium glutamate, lithium glutamate, cesium glutamate, rubidium glutamate, triethanolamine glutamate, monoethanolamine glutamate, diethanolamine glutamate, triisopropanolamine glutamate, arginine glutamate, lysine glutamate and the like. Most preferably, it is monosodium glutamate. The salt here encompasses solvates such as hydrate and the like.

The contact between glutamic acid or a salt thereof and the above-mentioned high-temperature high-pressure water varies depending on the solubility of glutamic acid or a salt thereof in the above-mentioned high-temperature high-pressure water, and is free of any particular limitation as long as glutamic acid or a salt thereof is homogeneously mixed with or dispersed in the above-mentioned high-temperature high-pressure water, which is exemplified by a solution in the above-mentioned high-temperature high-pressure water and slurry and paste in the above-mentioned high-temperature high-pressure water.

The mixing ratio of the glutamic acid or a salt thereof and the above-mentioned high-temperature high-pressure water is preferably such ratio as makes the content of glutamic acid or a salt thereof as a dry product 10–80 wt %, particularly 30–60 wt %.

The reactor need only be capable of maintaining the reaction for the necessary time under the above-mentioned temperature and pressure conditions. For example, it may be a batch type reactor using an autoclave and the like or a continuous type reactor using a tubular reactor and the like. For a simple structure, the reaction is preferably carried out by feeding with pressure a solution or slurry of glutamic acid or a salt thereof into a tubular reactor using a kneader or a pump. An example of the preferable apparatus to practice such method is shown in FIG. 1.

In FIG. 1, 1 is a high pressure pump, 2 is a reactor, 3 is a double pipe heat-exchanger, 4 is a drain valve, 5 is a back pressure valve, 6a and 6b are pressure gauges, 7 is a feed tank, 8 is a sampler, 9 is a safety valve and 10 is a heater. The starting material (a solution or slurry of glutamic acid or a salt thereof) in the feed tank (7) is fed to the reactor (2) with pressure by a high pressure pump (1). The reactor (2) is placed in the heater (10) to adjust the temperature of the internal reactor (2) to a given temperature. The pressure in the system (pressure from the delivery end of the high pressure pump (1) to the back pressure valve (5)) is adjusted to a given pressure by the back pressure valve (5). When the starting material passes through the reactor (2) adjusted to given temperature and pressure, self-cyclization of glutamic acid or a salt thereof occurs, thereby producing pyrrolidone carboxylic acid or a salt thereof. A reaction mixture containing the produced pyrrolidone carboxylic acid or a salt thereof is led to the double pipe heat-exchanger (3) equipped on the delivery end of the reactor (2) and rapidly cooled, whereby the reaction stops. Thus, the reaction time or residence time can be adjusted by the flow rate of the starting material fed by the high pressure pump (1).

The present invention is explained in detail in the following by referring to Examples. The present invention is not limited by these examples and can be modified within the technical scope of the invention disclosed in the foregoing and following description.

EXAMPLE 1

Production of Pyrrolidone Carboxylic Acid from L-glutamic Acid

Water was added to L-glutamic acid to prepare a 33 wt % dispersion. Using the apparatus of FIG. 1, this L-glutamic acid slurry was delivered by a high pressure pump (1) into a reactor (2) (stainless steel, cylindrical, inner diameter 3.87 mm) heated to 200° C. to start the reaction. The residence time, or the time of passage through the reactor (2), was controlled to be 100 sec when water alone was flown. By introducing into a double pipe heat-exchanger (3) equipped on the delivery end of the reactor (2) for rapid cooling, the reaction was stopped. The pressure was adjusted by a back pressure valve (5) in the system, thereby maintaining the pressure from the delivery end of the high pressure pump (1) to the back pressure valve (5) at 2 MPa.

The obtained reaction mixture was recovered as a solid after evaporating water. The produced pyrrolidone carboxylic acid and unreacted glutamic acid contained in the solid was redissolved and analyzed by a method using high performance liquid chromatography (hereinafter HPLC) (column; SUMIPAX PGODS 100-7 manufactured by SUMIKA CHEMICAL ANALYSIS SERVICE, LTD., column temperature; 40° C., eluent; 10 mM aqueous phosphoric acid solution, flow rate; 1 mL/min., detection; UV 210 nm) for quantitative determination.

The optical purity was determined by a method using HPLC (chiral column; SUMIPAX OA5500 manufactured by SUMIKA CHEMICAL ANALYSIS SERVICE, LTD., column temperature; 30° C., eluent; 2 mM aqueous copper sulfate solution:acetonitrile=95:5, flow rate; 1 mL/min., detection; UV 254 nm) for quantitative determination.

From the above-mentioned two analysis results, it was found that 96 wt % of pyrrolidone carboxylic acid and 3 wt % of unreacted glutamic acid were contained in the obtained solid. The optical purity of pyrrolidone carboxylic acid in an L/D ratio was 95/5. That is, the optical purity of the obtained L-pyrrolidone carboxylic acid was 90%.

EXAMPLE 2

Reaction Temperature Dependency

A dispersion of L-glutamic acid (33 wt %) was reacted in the same manner as in Example 1 except that the temperature was changed to 150° C.–250° C., the pressure was changed to 5 MPa, and the residence time was controlled to be 100 sec when water alone was flown.

Figure 2:
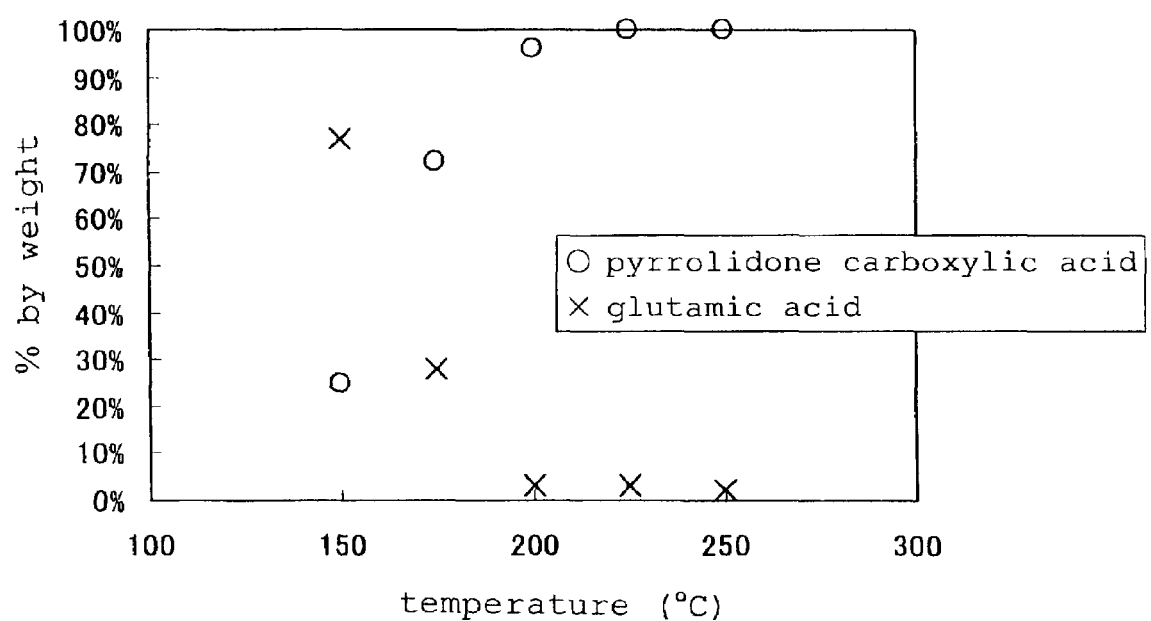
FIG. 2 shows the relationship between pyrrolidone carboxylic acid produced or residual glutamic acid, and the temperature (residence time 100 sec) in Example 1 and Example 2.

In the same manner as in Example 1, water was evaporated from the obtained reaction mixture to recover a solid, which was re-dissolved and analyzed by a method using HPLC to quantitatively determine pyrrolidone carboxylic acid and glutamic acid. The results are shown in FIG. 2.

EXAMPLE 3

Residence Time Dependency

A dispersion of L-glutamic acid (33 wt %) was reacted in the same manner as in Example 1 except that the temperature was changed to 200° C., the pressure was changed to 5 MPa and the residence time was controlled to be 30–300 sec when water alone was flown.

Figure 3:
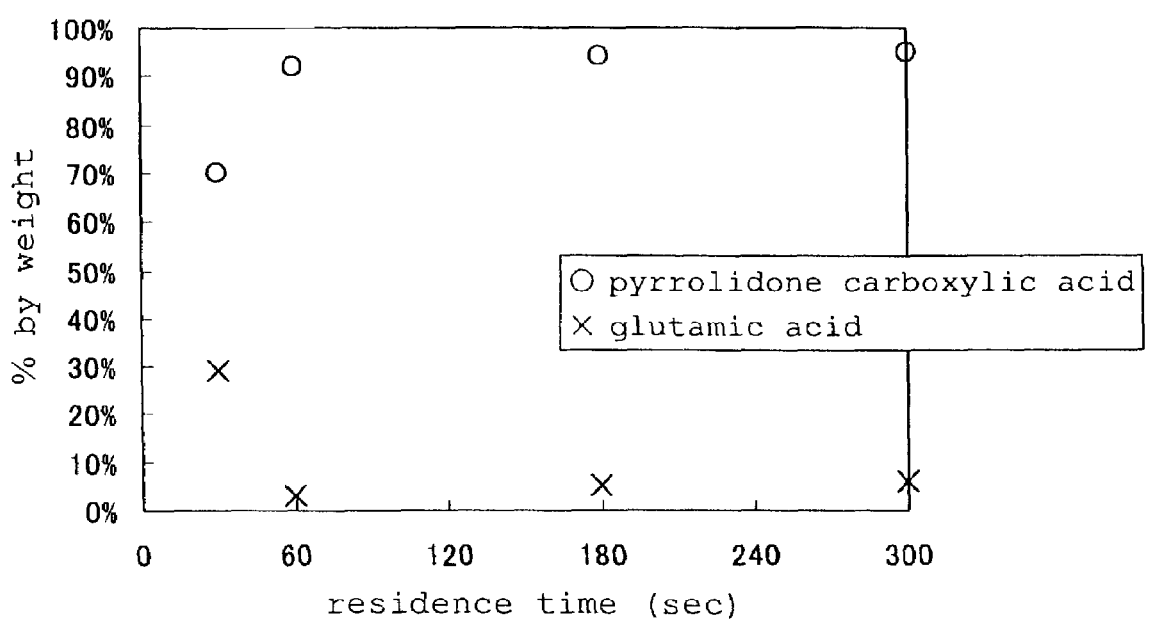
FIG. 3 shows the relationship between pyrrolidone carboxylic acid produced or residual glutamic acid, and the residence time (temperature 200° C.) in Example 3.

In the same manner as in Example 1, water was evaporated from the obtained reaction mixture to recover a solid, which was re-dissolved and analyzed by a method using HPLC to quantitatively determine pyrrolidone carboxylic acid and glutamic acid. The results are shown in FIG. 3.

EXAMPLE 4

Production of Sodium Pyrrolidone Carboxylate from Monosodium L-glutamate Monohydrate Water was added to monosodium L-glutamate monohydrate to prepare 43 wt % aqueous solution. This solution was reacted in the same manner as in Example 1, wherein the temperature was 200° C., the pressure was 5 MPa and the residence time was controlled to be 100 sec when water alone was flown.

The obtained reaction mixture was analyzed in the same manner as in Example 1 according to a method using HPLC and quantitatively determined for pyrrolidone carboxylic acid and glutamic acid. As a result, it was found that 88 mol % of the starting material had become pyrrolidone carboxylic acid and 12 mol % remained as glutamic acid.

COMPARATIVE EXAMPLE 1

Reaction of L-glutamic Acid Under Vapor Pressure

Figure 4:
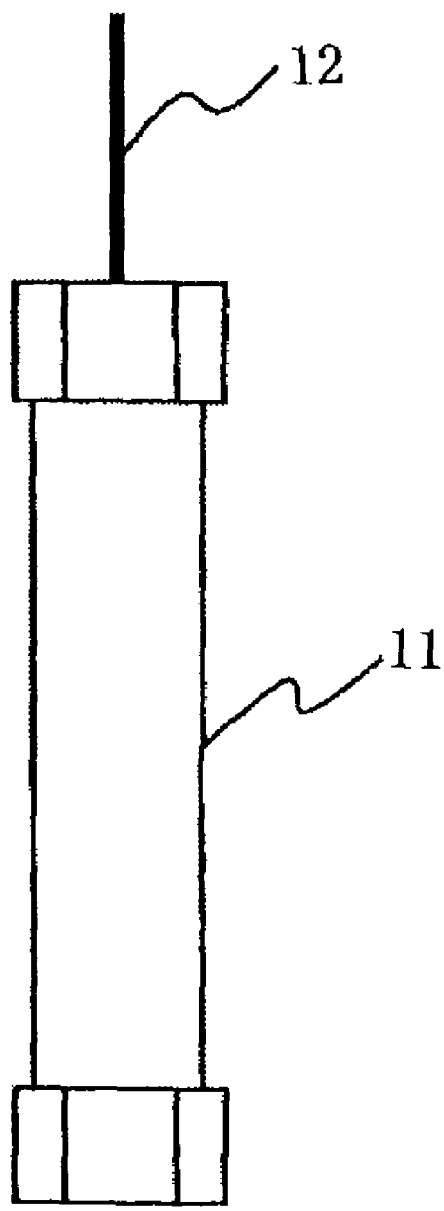
FIG. 4 is a schematic showing of the small container used in Comparative Example 1, wherein 11 shows a small container and 12 shows a temperature sensor (thermocouple).

L-Glutamic acid (1 g) and water (2 g) were cast in a small container (11) (inner diameter 6.23 mm, length 15 cm, content volume about 4.5 mL) shown in FIG. 4, and the container was cast in a hot bath at 200° C. The pressure then was 1.6 MPa (saturated vapor pressure of water at 200° C.). When 100 sec passed, the small container (11) was taken out (reaction time 100 sec) and immediately cooled with ice water to stop the reaction, and the contents were entirely recovered.

Water was evaporated from the recovered contents to give a solid, which was analyzed by HPLC as in Example 1. As a result, 32 wt % of pyrrolidone carboxylic acid and 67 wt % of unreacted glutamic acid were contained in the solid.

As mentioned above, the present invention affords efficient production and supply of pyrrolidone carboxylic acid or a salt thereof from glutamic acid or a salt thereof.

This application is based on a patent application No. 2001-219551 filed in Japan, the contents of which are hereby incorporated by reference.

What is claimed is:

1. A production method of pyrrolidone carboxylic acid or a salt thereof, which comprises contacting glutamic acid or a salt thereof with high-temperature, high-pressure water, wherein the reaction temperature ranges from 100° C. to 300° C., wherein said contacting is for a time ranging from 20 to 500 sec, and wherein said contacting is under an applied pressure which is greater than a the vapor pressure of water at said reaction temperature.

2. The production method of claim 1, wherein the glutamic acid or a salt thereof is an L-isomer, and the pyrrolidone carboxylic acid or a salt thereof is an L-isomer having optical purity of at least 80%.

3. The production method of claim 1, wherein said method is conducted continuously using a continuous type reactor.

4. The production method of claim 3, wherein a solution or slurry of glutamic acid or a salt thereof is fed under pressure into the continuous type reactor.

5. The production method of claim 1, wherein the applied pressure is 0.1 MPa to 25 MPa.

6. The production method of claim 1, wherein the applied pressure is 0.5 MPa to 10 MPa.

7. The production method of claim 1, wherein the reaction temperature ranges from 180° C. to 280° C.

8. The production method of claim 1, wherein the content of glutamic acid or salt thereof is 10 to 80 wt %.

9. The production method of claim 1, wherein the content of glutamic acid or salt thereof is 30 to 60 wt %.

10. The production method of claim 1, wherein said contacting is for a time ranging from 40 to 400 sec.

* * * * *